United States Patent
Chan

(10) Patent No.: US 10,473,638 B2
(45) Date of Patent: Nov. 12, 2019

(54) METHODS AND SYSTEMS FOR IMPROVING PRECISION OF MEASUREMENTS FOR REDUCED SAMPLE VOLUMES

(71) Applicant: Siemens Healthcare Diagnostics Inc., Tarrytown, NY (US)

(72) Inventor: Andy Chan, Franklin, MA (US)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 239 days.

(21) Appl. No.: 15/535,935

(22) PCT Filed: Dec. 17, 2015

(86) PCT No.: PCT/US2015/066350
§ 371 (c)(1),
(2) Date: Jun. 14, 2017

(87) PCT Pub. No.: WO2016/100648
PCT Pub. Date: Jun. 23, 2016

(65) Prior Publication Data
US 2017/0370900 A1  Dec. 28, 2017

Related U.S. Application Data

(60) Provisional application No. 62/094,604, filed on Dec. 19, 2014.

(51) Int. Cl.
*G01N 33/487* (2006.01)
*G01N 33/543* (2006.01)
*G01N 33/66* (2006.01)
*G01N 27/327* (2006.01)

(52) U.S. Cl.
CPC ........ *G01N 33/487* (2013.01); *G01N 27/327* (2013.01); *G01N 33/5438* (2013.01); *G01N 33/54393* (2013.01); *G01N 33/66* (2013.01)

(58) Field of Classification Search
None
See application file for complete search history.

(56) References Cited

U.S. PATENT DOCUMENTS 4,870,003 A * 9/1989 Kortright .......... G01N 33/54306
435/5
5,646,727 A * 7/1997 Hammer ............ F04B 43/1253
356/315

(Continued)

FOREIGN PATENT DOCUMENTS

WO  2009048977 A1  4/2009

OTHER PUBLICATIONS

International Search Report and Written Opinion of International Application No. PCT/US2015/066350 dated Feb. 25, 2016.

(Continued)

*Primary Examiner* — Christopher L Chin
(74) *Attorney, Agent, or Firm* — Dunlap Codding P.C.

(57) ABSTRACT

There is described a process for improving precision in an analytical test for a target analyte in a sample. The process includes prior to analyzing the sample for a target analyte via a biosensor, introducing to an analytical zone defined by the biosensor a fluid comprising an effective amount of the target analyte.

8 Claims, 6 Drawing Sheets

(56) References Cited

U.S. PATENT DOCUMENTS

| | | | |
|---|---|---|---|
| 7,469,606 B1 * | 12/2008 | Wiederin | G01N 1/38 73/864.24 |
| 8,062,491 B1 | 11/2011 | Gau | |
| 8,886,273 B2 | 11/2014 | Li et al. | |
| 2012/0172692 A1 | 7/2012 | Tamada et al. | |
| 2014/0370583 A1 | 12/2014 | Miller | |

OTHER PUBLICATIONS

European Search Report and Written Opinion of European Application No. 15871058.2 dated Sep. 7, 2017.

* cited by examiner

METHODS AND SYSTEMS FOR IMPROVING PRECISION OF MEASUREMENTS FOR REDUCED SAMPLE VOLUMES

The subject application claims benefit under 35 USC § 119(e) of U.S. Provisional Application No. 62/094,604, filed Dec. 19, 2014. The entire contents of the above-referenced patent application are hereby expressly incorporated herein by reference.

FIELD OF THE INVENTION

The invention relates to the field of diagnostic testing, and more particularly to processes and systems for improving precision in the measurement of one or more target analytes in a liquid sample with a reduced sample volume.

BACKGROUND OF THE INVENTION

Point-of-care testing refers generally to medical testing at or near the site of patient care such as in an emergency room. A desired outcome of point-of-care testing is to obtain rapid and accurate lab results to determine a next course of action in patient care. Instruments such as blood gas analyzers and critical care analyzers provide analytical results for a number of different analytes in a relatively short amount of time, e.g., 2 minutes or less. These instruments may employ a disposable sensor assembly having a plurality of different sensors disposed thereon, each for detecting a target analyte in a sample, e.g., a blood sample, flowing thereover or thereby. The sensors may be suitable for the detection and/or quantification of various target analytes for the sample taken from the patient. Exemplary analytes include but are not limited to pH, carbon dioxide partial pressure ($pCO_2$), oxygen partial pressure ($pO_2$), sodium ($Na^+$), potassium ($K^+$), calcium ($Ca^{2+}$), chloride ($Cl^-$), hematocrit (Hct), hemoglobin (Hb), glucose, lactate, bilirubin, CO-oximetry fractions ($fO_2Hb$, $fCO_2Hb$, $fMetHb$, $fHHb$), and the like.

Currently, there is an increasing demand for instruments that provide accurate and precise diagnostic results with reduced sample volumes (e.g., 100 µl or less). Reduced sample volumes are advantageous when limited sample is available from a patient, and in that they may leave further sample for other testing and/or may extend instrument, component, and accessory lifetimes of instruments using the same. Nevertheless, significant work is still needed as precision, accuracy, and consistency remain significant issues with the use of reduced sample volumes in diagnostic testing.

BRIEF DESCRIPTION OF THE DRAWINGS

The invention is explained in the following description in view of the drawings that show.

DETAILED DESCRIPTION OF THE INVENTION

Figure 1:
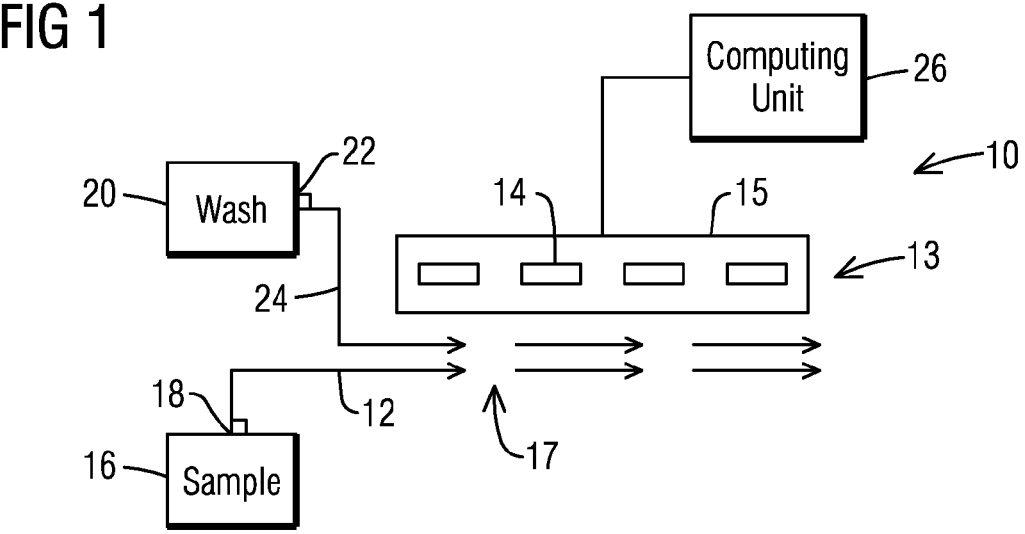
FIG. 1 illustrates a system for improving precision of a diagnostic assay in accordance with an aspect of the present invention.

Without wishing to be bound by theory, the present inventor has found that when analyzing reduced volume sample sizes, precision, accuracy, and consistency are impacted by one or both of reagent carryover and the small amount of aqueous components within the total sample volume. First, reagent carryover remains a significant problem when utilizing reduced sample volumes in certain diagnostic testing systems as the reduced sample volume may often be insufficient to fully displace pre-existing fluid in the system, e.g., the fluid in "an analytical zone" for a given biosensor. The result of insufficient displacement of a pre-existing fluid (e.g., a wash fluid) by the sample may be unintended mixing of the sample with pre-existing fluid in the system. This may result in unacceptable precision, particularly at specific medical decision levels for certain target analytes.

Further, it is believed that the nature of a whole blood sample contributes to a lack of precision when dealing with reduced sample volumes. In particular, the aqueous component of a whole blood sample (e.g., plasma) is actually less than 100% of the total volume of the sample due to whole blood cell volume (e.g., the volume of red blood cells, white blood cells, etc.). Thus, an already reduced sample volume (e.g., 75 µL) of whole blood may actually have a smaller volume of aqueous components than the 75 µL total blood volume. Certain sensors in a given sensor assembly therefore may have insufficient volume of the aqueous components of the whole blood sample to accurately test for target analytes. As a result, the introduction of a reduced volume whole blood sample may be insufficient to displace the pre-existing fluid within the analytical zone for a given sensor.

In accordance with one aspect of the present invention, the present inventor proposes introducing a fluid comprising an effective amount of the target analyte itself into an analytical zone of a sensor assembly (which comprises at least one biosensor configured for detecting the same target analyte) within a diagnostic system, wherein the biosensor will at least come into contact with the sample suspected of having the targeted analyte. The analytical zone is that volume of a sample within the detectable reach of the biosensor. In an embodiment, the delivery of the fluid comprising the target analyte to the analytical zone occurs prior to the delivery of a sample suspected of having the target analyte. Upon contact with the sample, the fluid enhances the precision of the assay, particularly in assays with reduced sample volumes, relative to a fluid without the target analyte. In an embodiment, the target analyte is provided in a wash fluid which is introduced into the system to clear away any previously introduced sample or reagents in the system which are exposed to an associated biosensor. In other embodiments, the fluid comprising the target analyte may be incorporated within a cartridge pre-packaged for shipment.

In accordance with another aspect of the present invention, there is provided a process for improving precision in a diagnostic test. In the process, a sample suspected of having a target analyte therein comes in contact with an amount of a fluid comprising an amount of the target analyte prior to analysis of the sample for the target analyte by a biosensor. The contacting between the fluids is effective to increase a degree of precision in the analysis for the target analyte relative to a fluid without the target analyte. The process is especially of use with reduced volume samples as the presence of the target analyte in the fluid is effective to improve the accuracy, precision, and reproducibility of the detection of the target analyte in such reduced volume samples.

In accordance with another aspect of the present invention, there is provided a process for improving precision in a diagnostic test. The process comprises delivering a first sample to an analytical zone of a biosensor for determination of an amount of a target analyte in the first sample. The process further comprises introducing into the analytical zone a fluid comprising an effective amount of the target analyte. Still further, the process comprises after the introducing of the first sample, delivering a second sample to an analytical zone of the sensor for determination of an amount of a target analyte in the second sample. Thus, the fluid acts as a wash fluid for rinsing away any pre-existing fluid in the analytical zone of the biosensor. Further, the target analyte in the wash fluid aids in improving accuracy and precision for the results of the analysis of the second sample by reducing or eliminating negative effects of any carryover of the fluid to the second sample.

The present inventor has found that the proposed solutions described herein are particularly suitable with the use of biosensors. Biosensors detect at least one analyte in a sample by using at least one biological detection material such as an enzyme, a receptor, and/or an antibody. Thus, in one embodiment, any one or more of the sensors described herein may comprise a biosensor that includes an effective amount of one or more enzymes for the target analyte of interest. The enzyme(s) will react with the target analyte (or breakdown product thereof) to directly or indirectly form a measurable analyte. By way of example, the biosensor may be one suitable for the analysis of glucose, lactate, or creatinine in a sample. In a particular embodiment, the sensor comprises a glucose biosensor as is known in the art. By way of example, glucose biosensors utilize the enzyme glucose oxidase to break down glucose and form a by-product of hydrogen peroxide. Thereafter, the hydrogen peroxide is oxidized by the electrode and the resulting current is a measure of the concentration of glucose. The use of a fluid as described herein with a biosensor is counter-intuitive to conventional thought in the art that the continuous use of the enzyme would lead to poor use life. However, this was shown not to be true as described below and shown in FIG. 8 herein.

As used herein, the term "analytical zone" refers to the volume considered and/or required for a given sensor to detect a predetermined analyte.

As used herein, the term "about" refers to a value that is ±10% of the stated value.

As used herein, the term "effective amount" means an amount necessary to bring about an intended result.

As used herein, the term "precision" means the extent to which a given set of measurements (>2) of the same sample agree with their mean.

As used herein, the term "target analyte" means a specific compound or combination of compounds in a fluid or sample fluid intended to be detected.

As used herein, the term "sensor" means a device that is able to detect at least one analyte in a sample.

As used herein, the term "sensor assembly" refers to a substrate comprising one or more sensors disposed across the substrate.

As used herein, the term "subject" refers to any human or non-human mammal.

Referring now to the figures, FIG. 1 illustrates a device 10 for analyzing one or more samples 12 for one or more target analytes. In certain embodiments, the device 10 comprises a point of care analyzer or a blood gas analyzer as is known in the art. Exemplary point of care analzyers are available from Siemens Healthcare Diagnostics, Inc. and are currently sold under the trademarks: RAPIDLab 1200, RapidLab 348EX, RAPIDPoint 500, RAPIDLab 248/348, RAPID-Point 400/405, and RAPIDPoint 340/350 Systems. Other commercially available point of care instruments are available from Roche Molecular Systems Inc., Medica Corp., Radiometer Medical (Denmark), and Nova Biomedical Corp.

For the analysis of the one or more samples 12 (hereinafter sample 12), the device 10 includes a sensor assembly 13 comprising one or more biosensors 14 (hereinafter "biosensor 14") for detecting one or more target analytes 30 (hereinafter "target analyte 30") suspected of being in the sample 12. The sensor assembly 13 may be integrated into the device 10 or may otherwise be removable/disposable. In the embodiment shown, the device 10 further includes a sample source 16, a first delivery mechanism 18 for delivering the sample 12 from the sample source to a flow path 17 flowing over and/or by the biosensor 14, a fluid source 20, and a second delivery mechanism 22 for delivering a fluid 24 comprising the target analyte 30 (corresponding to the same target analyte(s) suspected of being in the sample 12) from the fluid source 20 to the flow path 17. In an alternative embodiment, the sample 12 may be introduced into the sensor assembly 13 prior to the insertion of the sensor assembly 13 into the device 10. The sensor assembly 13 or biosensor 14 may be in direct or indirect communication with a computing unit 26 which may collect, store, and analyze analytical test results from the sensors 14 according to known methods. Referring to the embodiment of FIG. 1, after delivery of a first sample 12 to the sensor 14, the device 10 may introduce the fluid 24 to the flow path 17 from the fluid source 20 to clear the sample 12 from the sensor assembly 13 (or portion thereof) and prepare the device 10 for introduction of a subsequent sample, typically of the same type as the first sample 12.

The sample 12 to be introduced to the device 10 may comprise any biological material taken from a subject, for example, such as a bodily fluid, infection, or abscess collected from the subject by suitable methods and devices known in the art. Bodily fluids include but are not limited to urine, whole blood, blood serum, blood plasma, saliva, cerebrospinal fluid, pleural fluid, dialysate fluid, nasopharyngeal swabs, vaginal swabs, tears, tissues, and the like. The sample may further include any suitable buffers, diluents, or the like as are needed or desired for the particular type of sample. In particular embodiments, the sample 12 comprises a blood sample, which may be: a whole blood sample comprising plasma and whole blood cells; a plasma sample; or a serum sample. In a particular embodiment, the sample comprises a whole blood sample. The whole blood sample may comprise red blood cells, platelets and the like. In other embodiments, the blood sample comprises a plasma sample. To obtain the plasma sample, the sample may be one which has been treated to remove a plurality of the whole blood cells using known methods and components such as centrifugation or commercially available porous membranes.

The amount of sample 12 introduced to the device 10 may be any suitable volume. The sample may be introduced via a delivery mechanism (e.g., first delivery mechanism 18) which may comprises any suitable manual or automated fluid delivery system as is known in the art such as via an automated pipetting system or a syringe. In particular embodiments, the volume of the sample 12 is a reduced sample volume. The reduced sample volume may be about 100 µL or less, such as from 30 µL to 40 µL, 45 µL to 55 µL, 60 µL to 90 µL, or 75 to 85 µL.

The biosensor 14 may be one that is suitable for the qualitative, semi-quantitative, or quantitative determination for the presence of a target analyte 30 in a sample. As mentioned above, the biosensor 14 may be utilized to determine at least one analyte in a sample by using at least one biological detection material such as an enzyme, a receptor, and/or an antibody. When more than one sensor is present, the sensors which include at least one biosensor are arranged in a predetermined orientation such that as a given sample 12 travels along the flow path 17, the sample 12 is "met" by one sensor after the other at an "analytical zone" for each sensor, which will be described in further detail below. The analytical zone may be understood to refer to the volume which a biosensor 14 utilizes to detect a presence of a target analyte 30 for which it is intended. In an embodiment, the sensors may be disposed in a disposable, sealed measurement cartridge as is known in the art, which may also comprise the necessary calibration materials for the sensor. Such cartridges are commercially available from Siemens Healthcare Diagnostics, Inc. and are typically removably insertable into the device 10. In certain embodiments, the calibration materials are also spiked with the target analyte 30.

The biosensor 14 may be any suitable sensor known in the art configured to provide a parameter indicative of an amount of one or more of a target analyte 30 such as glucose, lactate, and creatinine in the sample 12. In turn, the fluid 24 may comprise an amount of the target analyte 30 detectable by the biosensor 14 such as glucose, lactate, and creatinine. The amount of the target analyte 30 in a sample may be determined qualitatively, semi-quantitatively, or quantitatively from the data provided from the sensor 14 through the use of known standards and controls as would be well understood by persons skilled in the art. For example, results may be compared to values of a calibration curve created from a plurality of standard samples having predetermined concentrations as is well-known in the art. In certain embodiments, the biosensor 14 may be utilized to determine whether the presence of a target analyte 30 in the sample 12 is above or below a predetermined threshold value.

Figure 2:
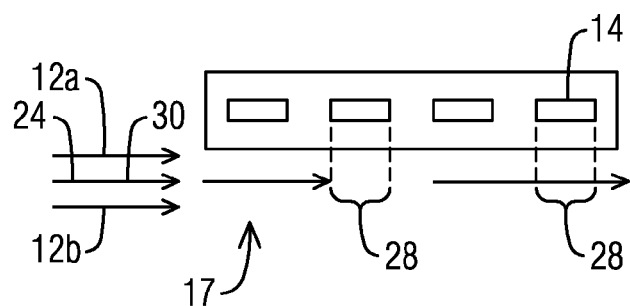
FIG. 2 illustrates a sensor defining an analytical zone in accordance with an aspect of the present invention.

Referring to FIG. 2, there is shown a portion of a flow path 17 traveling past the sensors 14. As shown, the portion of the flow path 17 that is exposed to the sensor may be referred to as the "analytical zone 28." In this embodiment, the analytical zone 28 is shown as having a substantially rectangular shape; however, it is understood that the present invention is not so limited. Regardless, in an embodiment, a delivery mechanism 18 (FIG. 1) may deliver a first sample 12a to the flow path 17 which flows past the sensors. Thereafter, a delivery mechanism 22 delivers a fluid 24 to the flow path 17 to eliminate any carryover of the first sample 12a prior to introduction of a subsequent sample (shown as 12b) to the flow path 17. As can be appreciated, if the volume of the second sample 12b is insufficient to displace the amount of fluid 24 present in the analytical zone 28, then the fluid 24 will be mixed with the second sample 12b and may alter the analytical results via the unintended mixing. For example, the second sample 12b could be diluted, thereby providing a result for a target analyte that is misrepresentative of the actual value for the target analyte. Typical prior art use of biosensors solely introduce a wash fluid free of the target analyte.

In accordance with an aspect of the present invention, however and in contrast to prior art systems and processes, the fluid 24 described herein actually comprises an amount of a target analyte 30 for which the biosensor 14 is configured to determine a presence of. The fluid 24 is flowed through the flow path 17 and the analytical zone 28 prior to the introduction of a sample 12 to the flow path 17 and the analytical zone 28. In this way, the fluid 24 will be in fluidic contact with a sample 12 subsequently delivered to the flow path 17 and the analytical zone 28.

The proposed solution of incorporating an amount of the target analyte 30 in a fluid and delivering the same to the analytical zone 28 of a given sensor 14 prior to introduction of a sample 12 thereto is particularly counterintuitive. The conventional thought in the art is or would have been that use of the target analyte in of itself in a wash fluid immediately before introduction of a sample would produce inaccurate analytical results and further would rapidly decrease the use life of the associated biosensor 14 as the device 10 would be adding significant exposure of the sensor 14 to the target analyte, thereby resulting in the reduced use life. The present inventor has surprisingly found, however, and shown (see Examples also below) that the delivery of a fluid 24 comprising a target analyte 30 to the analytical zone 28 of a respective biosensor 14 immediately prior to introduction of a sample 12 suspected of having the target analyte 30 to the same analytical zone 28 may significantly improve the precision of the assay for the target analyte 30 yet does not result in significant reduction in use life of the associated sensor. The fluid 24 (e.g., a wash fluid) comprising the target analyte 30 may eliminate the skewing of analytical results typically seen with the unintended mixing of fluid 24 with a sample 12 (e.g., reduced volume whole blood sample).

In an embodiment, the amount of the target analyte 30 in the fluid 24 is sufficient to provide at least a degree of improvement in precision in an associated assay for the target analyte. The associated assay is the one for which the target analyte 30 of the fluid 24 is intended to improve. Nevertheless, the amount of the target analyte 30 in the fluid 24 is preferably not so high that the assay for the target analyte 30 over-recovers as a result of carryover from the fluid 24 to a sample 12 introduced thereafter. If too high a concentration is utilized in the fluid 24, this would likely produce a higher than actual result for the target analyte upon analysis of the subsequent sample.

In one aspect, the concentration of the target analyte 30 may be included in the fluid 24 as a percentage of a predetermined minimum or a predetermined maximum threshold value against which a measured concentration of the target analyte in the sample will be compared. In a particular embodiment, the concentration of the target analyte 30 may be from 100-300% of the concentration of the predetermined minimum threshold value and from 25-75% of the predetermined maximum threshold value for the target analyte.

In another aspect, the predetermined threshold value may comprises a medical decision value, and an amount of the target analyte 30 in the fluid 24 is greater than a lower medical decision value and lower than an upper medical decision value for the target analyte 30. In certain embodiments, the concentration of target analyte 30 in the fluid 24 may be one that lies within a range for the target analyte 30 in the sample 12 such as between the medical decision values, e.g., from 25 to 75% of the medical decision values.

The fluid 24 comprising an amount of the target analyte 30 may be delivered to the analytical zone 28 from the fluid source 20 by the delivery mechanism 22, which may be an automated pipetting or dispensing system as is known in the art. In critical care analyzers or the like as are known in the art, it is common for wash reagents, for example, to be housed in a suitable vessel such as a pouch or bag formed from an inert material along with other such vessels for the storage of suitable reagents necessary for the assays to be performed. In an embodiment, the fluid source 20 may comprise one or more of these vessels, which is then housed in a cartridge. In certain embodiments, a separate cartridge may be provided for the wash fluid and the reagents.

The fluid 24 may be introduced to the analytical zone 28 prior to the introduction of a sample to the zone 28 or may be introduced to the analytical zone 28 between subsequently analyzed samples. It is understood that it is merely critical that an amount of a predetermined target analyte 30 is intentionally introduced to the analytical zone 28 in the fluid 24 prior to contact of a sample suspected of having the predetermined target analyte 30. In an embodiment, the fluid 24 may be present in the analytical zone 28 in a pre-packaged cartridge comprising a sensor assembly 13 and the fluid 24.

The fluid 24 may comprises an aqueous medium comprising the target analyte. Still further, the fluid may include suitable buffers, stabilizers, surfactants and the like as are known in the art for use in wash fluids. In certain embodiments, the fluid 24 is mixed with the target analyte prior to use in the device 10.

Figure 3:
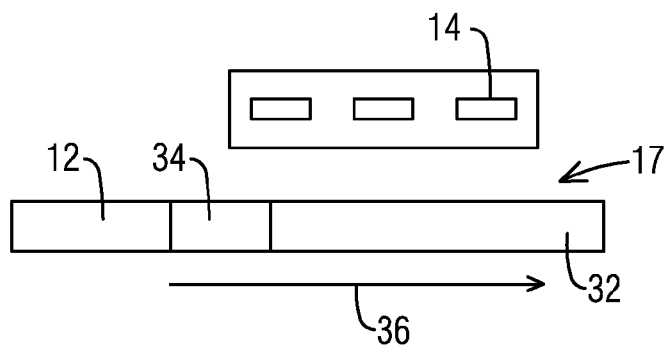
FIG. 3 illustrates an embodiment of a wash fluid for improving precision in accordance with an aspect of the present invention.

In another embodiment, as shown in FIG. 3, there is shown a first portion 32 which is a fluid free from the target analyte and a slug 34 which comprises the target analyte. In this embodiment, prior to the delivery of a sample 12 to the analytical zone, a wash reagent 32 as is typical in the art with no target analyte is flowed through the flow path 17 in the direction of arrow 36. Just prior to the introduction of a sample 12, the slug 34 comprising the target analyte 30 may be delivered to the analytical zone 28 from a suitable source and delivery mechanism as was described herein with respect to other fluids. In certain embodiments, the slug 34 may have a volume which is less than the volume of the analytical zone 28. Further, the slug 34 may have a similar concentration of the target analyte as was described for a mixed wash fluid, but may have a lesser volume. Since it is the portion of the fluid that interfaces with the subsequently delivered sample which is of importance, the slug 34 is sufficient to bring about the desired effects of improving precision of the assay of the subsequent sample for a target analyte.

It is understood that the target analyte 30 to be utilized in the fluid 24 is without limitation. It is understood however that a sensor 14 is typically provided for detection of the target analyte 30. In addition, it is understood that the fluid 24 may comprise more than one target analyte 30 as the sensor assembly 13 may comprise a plurality of sensors 14 for the detection of more than one target analyte.

In another aspect, the fluid 24 comprising an amount of the target analyte 30 as described herein may be pre-loaded within a single use disposable cartridge for use in a device 10 such as a point of care analyzer. The disposable cartridge may comprise the fluid 24 along with at least one biosensor 14 or a sensor assembly 13 as are described herein. The sample 12 suspected of having the target analyte may be added to the cartridge internally or externally of the device 10. The fluid 24 in the cartridge comprising an amount of the target analyte 30 may be added to the sample 12 in a volume and concentration which effective to improve precision of the analysis for the target analyte 30. The disposable cartridge comprising a sensor assembly 13 or biosensor 14 may be prepared for shipment in a suitable packaging such as a sealed, air tight pouch formed from an inert material as is known in the art.

In a particular embodiment, the target analyte 30 described herein may be glucose. In certain embodiments, the typical lower and upper medical decision values for glucose are 50 mg/dL and 200 mg/dL, respectively. By way of example only, the present inventor has found that a wash solution comprising 75 mg/dL of glucose met desired precision specifications at both medical decision levels (50 mg/dL and 200 mg/dL) at reduced sample volumes (65 µL sample) when used in a process as described herein.

Referring again to FIG. 1, the computing unit 26 comprises one or more modules configured to receive data from one or more sensors 14 and determine a result from the data. The result may be a qualitative, semi-quantitative, or quantitative amount of one or more target analytes 30. The computing unit 26 may be integrated within the device 10 or may be independent thereof and in wired or wireless communication therewith. In addition, the computing unit 26 may comprise, for example, a special purpose computer comprising a microprocessor, a microcomputer, an industrial controller, a programmable logic controller, a discrete logic circuit or other suitable controlling device. In an embodiment, the computing unit 26 may further comprise one or more input channels, a memory, and output channel(s). The memory may include a computer-readable medium or a storage device, e.g., floppy disk, a compact disc read only memory (CD-ROM), or the like. In an embodiment, the computing unit 26 may comprise computer readable instructions for performing any aspect of the methods or for controlling any aspect of the components described herein.

Examples are provided hereinbelow. However, it is understood that the description herein is not to be limited in its application to the specific experimentation, results, and laboratory procedures. Rather, the Examples are simply provided as one of various embodiments and are meant to be exemplary, not exhaustive.

NON-LIMITING EXAMPLES

Example 1

Wash reagent bags were made with 75, 125 and 200 mg/dL of glucose. These were built up into wash/waste cartridges and installed on reduced sample volume (RSV) systems. For each glucose wash concentration, two runs of Level 1 blood (glucose with 50 mg/dL) were run in triplicate in Normal Syringe Mode (200 µL) and in Microcap Mode (65 µL). Additionally, two runs of Level 4 blood (glucose with 200 mg/dL) were run in triplicate in Normal Syringe Mode (200 µL) and in Microcap Mode (65 µL).

Figure 4:
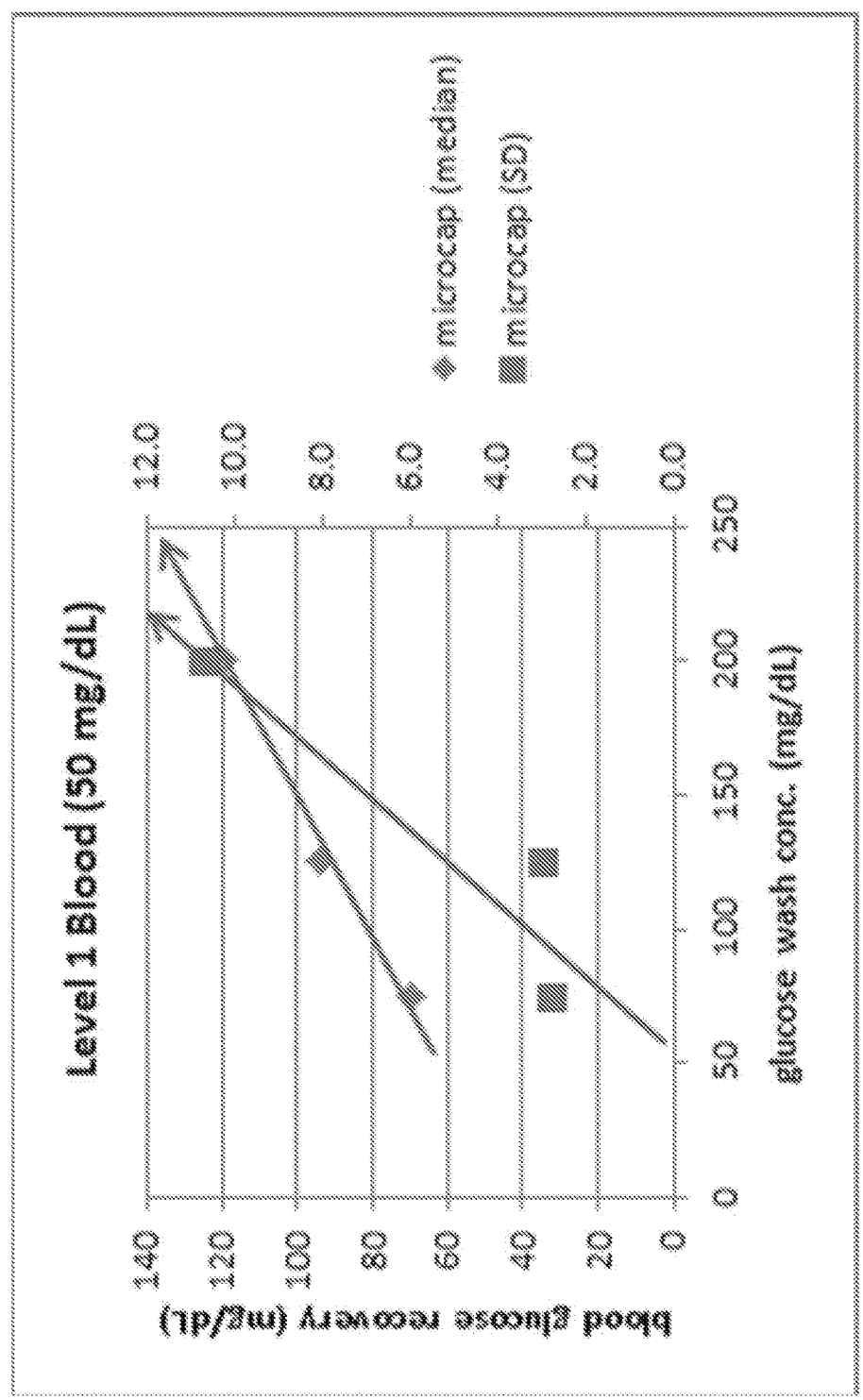
FIG. 4 illustrates blood glucose recovery and glucose precision (standard deviation) vs. glucose wash concentration for reduced sample volumes (65 µL) of blood with a glucose concentration of 50 mg/dL
Figure 5:
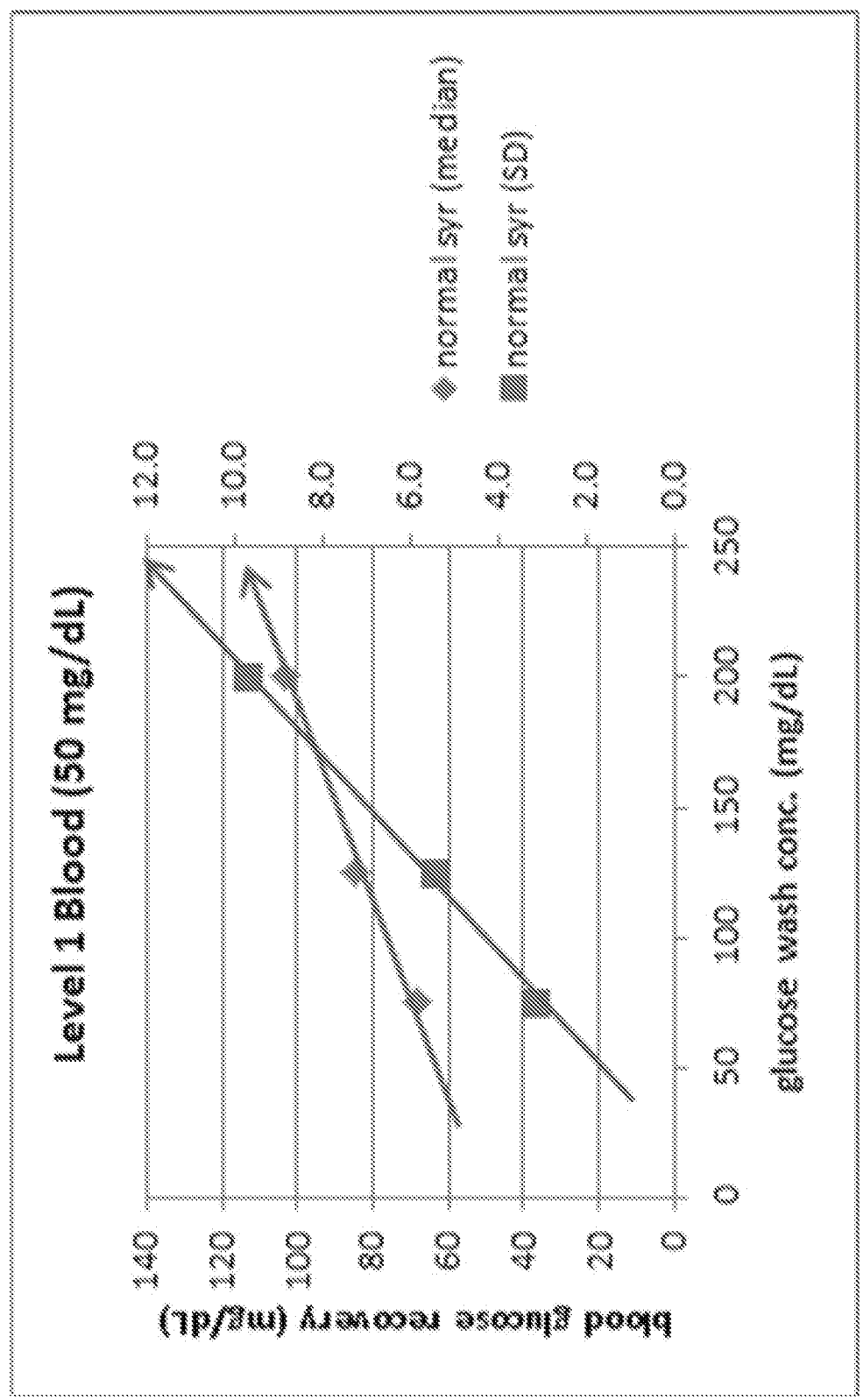
FIG. 5 illustrates blood glucose recovery and glucose precision (standard deviation) vs. glucose wash concentration for normal volumes (200 µL) of blood with a glucose concentration of 50 mg/dL.

Data was post-processed for each sample using signals from two calibration points. The first calibration point was determined from an aqueous reagent containing 200 mg/dL of glucose. The second calibration point was determined by using zero glucose concentration for the electronic zero offset of the instrument. No other algorithms were applied to the raw data. Whole blood precision was determined as the standard deviation (SD) of the post-processed glucose concentration by level and by sample mode (i.e Normal Syringe Mode or Microcap Mode). The results for Level 1 blood (glucose with 50 mg/dL) are shown in FIG. 4-5 for both microcap and normal syringe modes. The diamond-shaped points correspond to the glucose recovery (mg/dL) and are associated with the left-side vertical axis. The square-shaped points correspond to the glucose SD precision and are associated with the right-side vertical axis.

For the results shown in FIGS. 4-5, it can be seen that as the glucose wash concentration moves away and above the target blood concentration of 50 mg/dL that the glucose result over-recovers as a result of carryover of the glucose in the wash into the blood sample. Additionally, the blood precision worsens as the glucose wash concentration moves away and above the target blood concentration. This is a result of a greater impact of inconsistent wash carryover at wash concentrations farther away from the target blood concentration. These effects are seen in both Microcap and Normal Syringe modes; however, both effects appear more pronounced at the lower reduced sample volumes than the higher Normal Syringe volumes.

Figure 6:
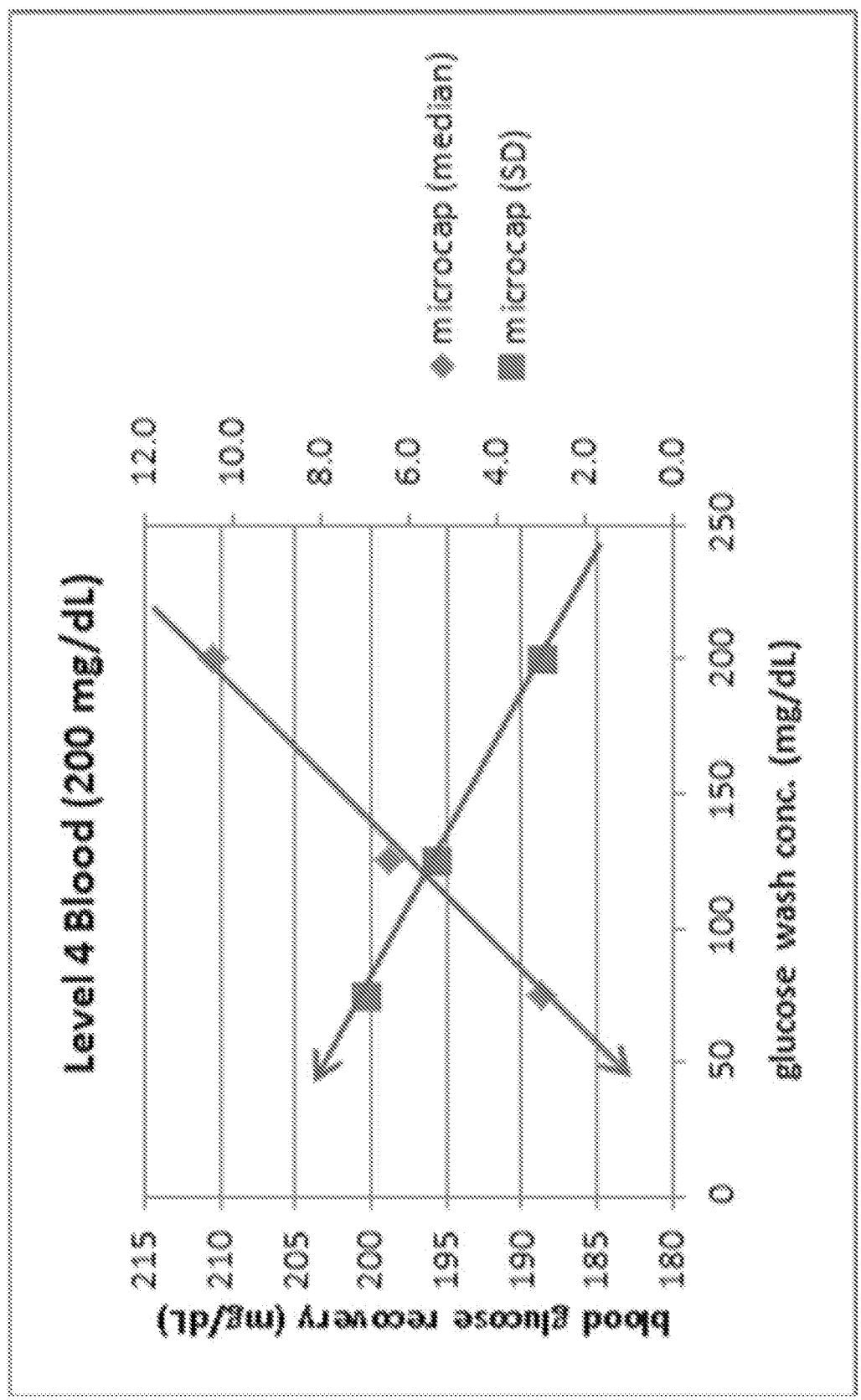
FIG. 6 illustrates blood glucose recovery and glucose precision (standard deviation) vs. glucose wash concentration for reduced sample volumes (65 µL) of blood with a glucose concentration of 200 mg/dL.
Figure 7:
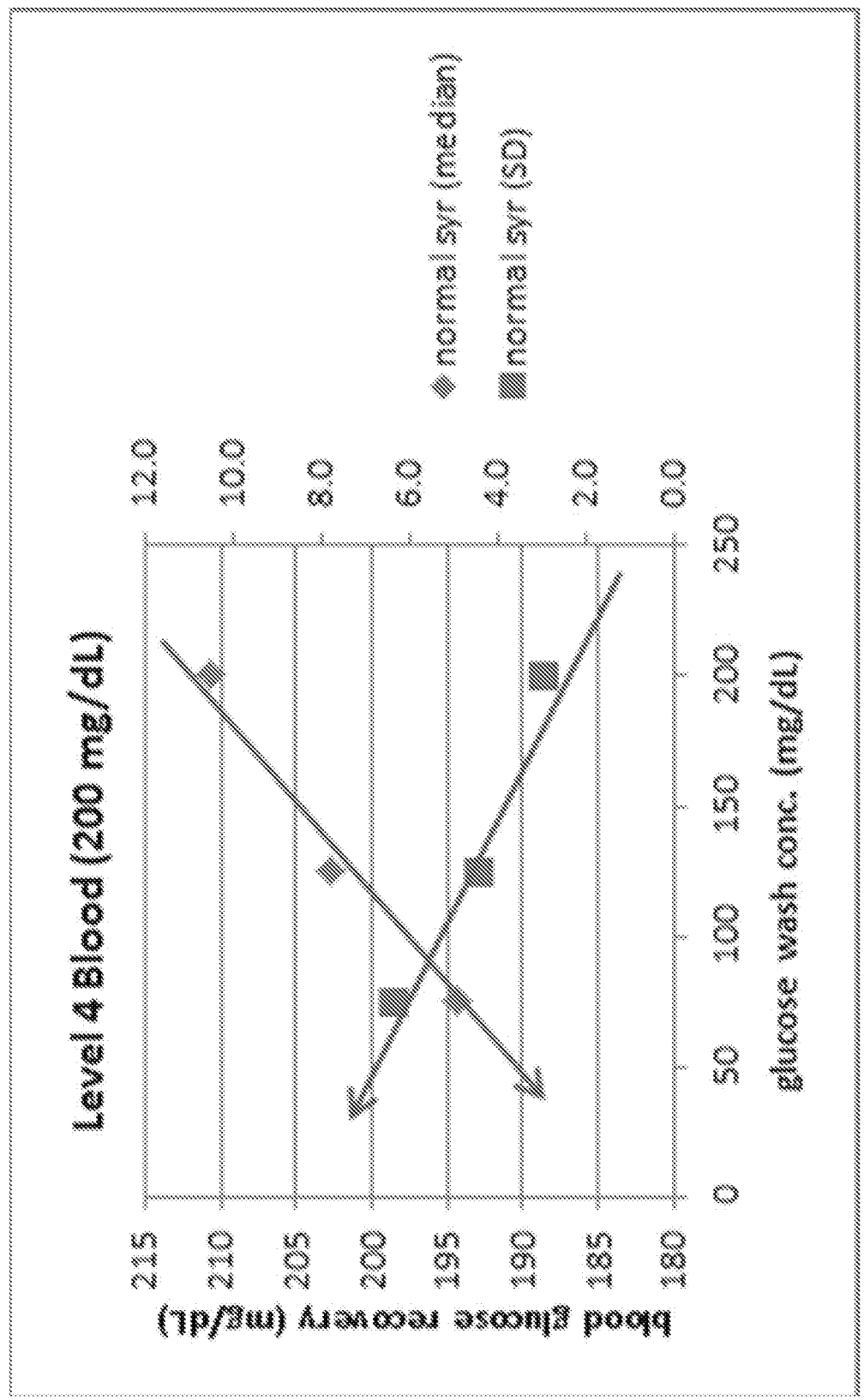
FIG. 7 illustrates blood glucose recovery and glucose precision (standard deviation) vs. glucose wash concentration for normal volumes (200 µL) of blood with a glucose concentration of 200 mg/dL.

Similarly, the results for the Level 4 blood (glucose with 200 mg/dL) are plotted for both Microcap and Normal Syringe modes in FIGS. 6-7. For FIGS. 6-7, it can readily be seen that as the glucose wash concentration moves away and below the target blood concentration of 200 mg/dL, the glucose result under-recovers as a result of wash reagent dilution of the blood sample. Additionally, the blood precision gets worse as the glucose wash concentration moves away and below the target blood concentration. This is a result of a greater impact of inconsistent wash carryover at wash concentrations farther away from the target blood concentration. These effects are seen in both Microcap and Normal Syringe modes, however, both effects appear slightly more pronounced at the lower RSV sample volume as would be expected with the proposed mechanism.

The figures showing the Microcap mode (FIGS. 4 and 6) illustrate that the 75 mg/dL wash concentration is a good compromise and provides good whole blood precision results at both medical decision levels.

In conclusion, it was found that wash reagent with 200 mg/dL glucose provided excellent Level 4 blood precision, however, it resulted in poor Level 1 blood precision.

Conversely, a lower concentration of glucose wash (e.g. zero mg/dL) provided better Level 1 blood precision at the expense of poorer Level 4 blood precision. A glucose wash concentration of 75 mg/dL was found to provide a good compromise for both the Level 1 and Level 4 blood levels. With a glucose wash concentration of 75 mg/dL, the precision at both 50 and 200 mg/dL levels of blood was within acceptable limits using a 65 µL RSV sample volume.

Results from this experiment show the glucose wash concentration to be a significant factor to the whole blood precision and to the whole blood recovery for both Microcap and Normal Syringe modes. This is consistent with the proposed mechanism of inconsistent wash reagent carryover to the blood sample.

Example 2

Figure 8:
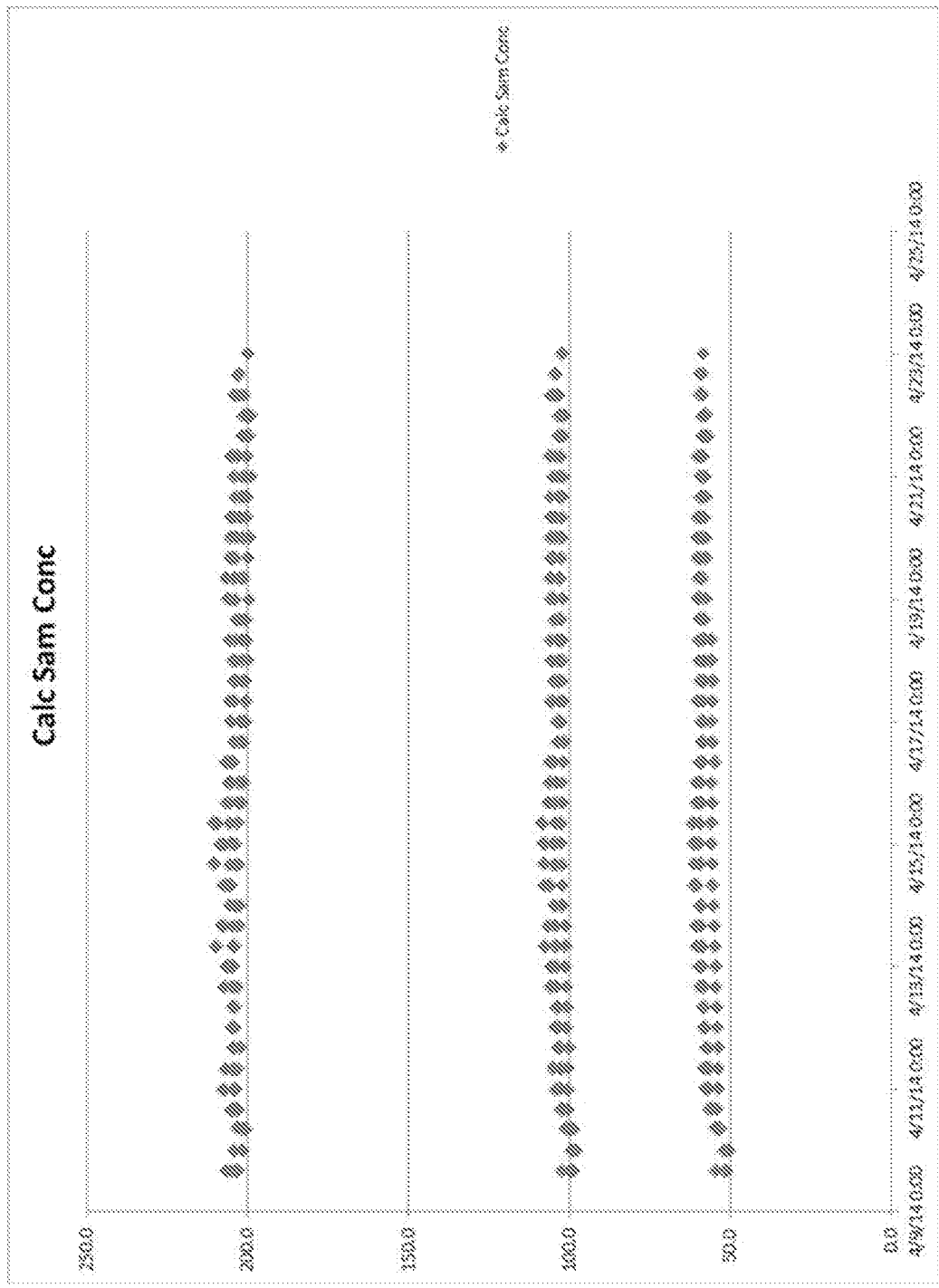
FIG. 8 illustrates the stability of glucose sensor recovery over time even with repeated use of a glucose wash in accordance with an aspect of the present invention.

In this experiment, as shown in FIG. 8, it was shown that repeated exposure of the sensor to a wash reagent comprising an amount of the target analyte such as glucose, in fact, did not degrade sensor performance and use life over a span of 2 weeks. Wash reagent was prepared with a high concentration (200 mg/dL) of glucose. This wash reagent was continuously exposed to the glucose sensor throughout the entire study. At every 8 hour intervals, the performance of the glucose sensor was tested by measuring the recovery of aqueous solutions containing 50, 100 and 200 mg/dL of glucose.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

The following is a numbered list of non-limiting, illustrative embodiments of the inventive concepts disclosed herein:

1. A process for improving precision in a diagnostic test utilizing a biosensor comprising: contacting a sample suspected of having a target analyte therein with an amount of a fluid comprising an amount of the target analyte prior to analysis of the sample for the target analyte; wherein the contacting is done within an analytical zone defined by the biosensor, the biosensor configured for detection of a presence of the target analyte; and wherein the contacting is effective to increase a degree of precision in the analysis for the target analyte.

2. The process of illustrative embodiment 1, wherein the sensor is configured for the determination of a presence of a member selected from the group consisting of glucose, lactate, and creatinine.

3. The process in any of illustrative embodiments 1 to 2, wherein the fluid comprises a wash fluid which is delivered to the analytical zone prior to delivery of the sample to the analytical zone.

4. The process in any of illustrative embodiments 2 to 3, wherein the fluid comprises a slug comprising the target analyte, wherein the slug is delivered to the analytical zone following delivery of a wash fluid without the target analyte through the analytical zone and prior to introduction of the sample through the analytical zone.

5. The process in any of illustrative embodiments 1 to 4, wherein the fluid comprises an amount of the target analyte greater than a lower medical decision value and lower than an upper medical decision value for the target analyte.

6. The process in any of illustrative embodiments 1 to 5, wherein the target analyte is selected from the group consisting of glucose, lactate, and creatinine.

7. The process of illustrative embodiment 6, wherein the target analyte comprises glucose.

8. The process of illustrative embodiment 7, wherein the fluid comprises from 50 mg/dL to 200 mg/dL of glucose.

9. The process of illustrative embodiment 8, wherein the fluid comprises from 75 mg/dL to 125 mg/dL of glucose.

10. The process in any of illustrative embodiments 1 to 9, further comprising analyzing the sample for a presence of the target analyte.

11. The process in any of illustrative embodiments 9 to 10, wherein the sample comprises a reduced sample volume of less than 100 µL.

12. The process in any of illustrative embodiments 10 to 12, wherein the sample comprises a reduced sample volume of from 25 µL to 75 µL.

13. The process in any of illustrative embodiments 10 to 12, wherein the analyzing the sample for a presence of the target analyte comprises determining whether an amount of the target analyte is at least one of greater than a lower medical decision value or lower than an upper medical decision value for the target analyte.

14. The process of illustrative embodiment 13, wherein the target analyte is glucose, and wherein the lower medical decision value is about 50 mg/dL of glucose and the lower medical decision value is 200 mg/dL of glucose.

15. The process of illustrative embodiment 14, wherein fluid comprises from 50 mg/dL to 200 mg/dL of glucose.

16. The process of illustrative embodiment 15, wherein the fluid comprises about 75 mg/dL of glucose.

17. The process in any of illustrative embodiments 1 to 16, wherein the fluid is less than 100 µL in volume.

18. The process of illustrative embodiment 1, wherein the fluid comprises an amount of a first target analyte and an amount of a second target analyte, and wherein after the contacting of the fluid with the target analytes, the process further comprises analyzing the sample in a first analytical zone defined by a first biosensor for a presence of the first target analyte and analyzing the sample in a second analytical zone defined by a second biosensor for a presence of the second target analyte.

19. The process in any of illustrative embodiments 1 to 18, wherein the contacting done between the analysis of two different samples suspected of having an amount of the target analyte.

20. The process in any of illustrative embodiments 1 to 19, wherein the process is carried out in a point of care analyzer.

21. The process in any of illustrative embodiments 1 to 20, wherein the sensor is disposed on a substrate comprising a plurality of additional sensors.

22. A process for improving precision in a diagnostic test comprising:
delivering a first sample to an analytical zone of a biosensor for determination of an amount of a target analyte in the first sample;
introducing into the analytical zone a fluid comprising an effective amount of the target analyte; and
biosensor for determination of an amount of a target analyte in the second sample.

23. The process of illustrative embodiment 22, wherein the fluid comprises a slug comprising the target analyte, wherein the slug is delivered to the analytical zone following delivery of a wash fluid without the target analyte to the analytical zone.

24. The process in any of illustrative embodiments 22 and 23, wherein the fluid comprises an amount of the target analyte greater than a lower medical decision value and lower than an upper medical decision value for the target analyte.

25. The process in any of illustrative embodiments 22 to 24, wherein the target analyte is selected from the group consisting of glucose, lactose, and creatinine.

26. The process of illustrative embodiment 25, wherein the target analyte comprises glucose.

27. The process of illustrative embodiment 26, wherein the fluid comprises from 50 mg/dL to 200 mg/dL of glucose.

28. The process of illustrative embodiment 27, wherein the fluid comprises from 75 mg/dL to 125 mg/dL of glucose.

29. The process in any of illustrative embodiments 22 to 28, wherein the first sample and the second sample comprise a reduced sample volume of less than 100 µL.

30. The process in any of illustrative embodiments 22 to 29, wherein the first sample and the second sample comprise a reduced sample volume of from 25 µL to 75 µL.

31. The process in any of illustrative embodiments 22 to 30, wherein the determination of an amount of a target analyte in the first and second sample comprises determining whether an amount of the target analyte is at least one of greater than a lower medical decision value or lower than an upper medical decision value for the target analyte.

32. The process of illustrative embodiment 31, wherein the target analyte is glucose, and wherein the lower medical decision value is about 50 mg/dL of glucose and the lower medical decision value is 200 mg/dL of glucose.

33. The process of illustrative embodiment 32, wherein the target analyte is glucose, and wherein the fluid comprises from 50 mg/dL to 200 mg/dL of glucose.

34. The process of illustrative embodiment 33, wherein the fluid comprises about 75 mg/dL of glucose.

35. The process in any of illustrative embodiments 22 to 34, wherein the fluid is less than 100 µL in volume.

36. The process in any of illustrative embodiments 22 to 35, wherein the process is carried out in a point of care analyzer.

37. The process in any of illustrative embodiments 22 to 36, wherein the sensor is disposed on a substrate comprising a plurality of additional sensors.

38. A system for improving for improving precision in a diagnostic test comprising:
a biosensor defining an analytical zone and configured for the detection of a target analyte;
a wash fluid source comprising a fluid, the wash fluid comprising an amount of the target analyte;
a first delivery mechanism in communication with the wash fluid source for introducing the wash fluid to the analytical zone;
a second delivery mechanism in communication with a sample suspected of comprising the target analyte for introducing the sample to the analytical zone following introduction of the wash fluid to the analytical zone;
wherein upon delivery of the wash fluid to the analytical zone and delivery of the sample, the amount of the target analyte in the wash fluid is effective to increase a degree of precision in the analysis for the target analyte in the sample.

39. The system of illustrative embodiment 38, wherein the biosensor is configured for the detection of a target analyte selected from the group consisting of glucose, lactate, and creatinine.

40. The system of illustrative embodiment 38, wherein the wash fluid comprises an amount of the target analyte greater than a lower medical decision value and lower than an upper medical decision value for the target analyte.

41. The system in any of illustrative embodiments 38 to 40, wherein the target analyte is selected from the group consisting of glucose, lactate, and creatinine.

42. The system of illustrative embodiment 41, wherein the target analyte comprises glucose.

43. The system of illustrative embodiment 42, wherein the fluid comprises from 50 mg/dL to 200 mg/dL of glucose.

44. The system of illustrative embodiment 43, wherein the fluid comprises from 75 mg/dL to 125 mg/dL of glucose.

45. The system in any one of illustrative embodiments 38 to 44, wherein the sample comprises a reduced sample volume of less than 100 µL.

46. The system of illustrative embodiment 45, wherein the sample comprises a reduced sample volume of from 25 μL to 75 μL.

47. The system in any one of illustrative embodiments 38 to 46, wherein the amount of the target analyte is at least one of greater than a lower medical decision value or lower than an upper medical decision value for the target analyte.

48. The system of illustrative embodiment 47, wherein the target analyte is glucose, and wherein the lower medical decision value is about 50 mg/dL of glucose and the lower medical decision value is 200 mg/dL of glucose.

49. The system of illustrative embodiment 48, wherein fluid comprises from 50 mg/dL to 200 mg/dL of glucose.

50. The system of illustrative embodiment 49, wherein the fluid comprises about 75 mg/dL of glucose.

51. The system in any one of illustrative embodiments 38 to 50, wherein the fluid is less than 100 μL in volume.

52. A disposable cartridge for use in a point of care instrument for analysis of a target analyte, the disposable cartridge comprising:
a fluid comprising an amount of the target analyte; and
at least one sensor con/figured for detection of the target analyte;
wherein the cartridge is stored within a container for shipment of the cartridge.

The invention claimed is:

1. A process for improving precision in a diagnostic test utilizing an enzymatic biosensor, the process comprising:
   delivering a fluid to an analytical zone of an enzymatic biosensor, wherein the fluid comprises an amount of the target analyte greater than a lower medical decision value and lower than an upper medical decision value for the target analyte;
   delivering a sample suspected of having a target analyte therein to the analytical zone of the enzymatic biosensor, whereby the sample contacts the fluid within the analytical zone prior to analysis of the sample for the target analyte;
   analyzing the sample for a presence of the target analyte by the enzymatic biosensor following contact of the sample with the fluid; and
   wherein the contact between the sample and the fluid is effective to provide at least a degree of improvement in precision in the analysis for the target analyte when compared to analysis without contact with the fluid.

2. The process in claim 1, wherein the fluid comprises a slug comprising the target analyte, wherein the slug is delivered to the analytical zone following delivery of a wash fluid without the target analyte through the analytical zone and prior to introduction of the sample through the analytical zone.

3. The process in claim 1, wherein the enzymatic biosensor is disposed on a substrate comprising a plurality of additional sensors.

4. A process for improving precision in a diagnostic test comprising:
   delivering a first sample to an analytical zone of an enzymatic biosensor for determination of an amount of a target analyte in the first sample;
   introducing into the analytical zone a fluid comprising an effective amount of the target analyte, wherein the effective amount of the target analyte is greater than a lower medical decision value and lower than an upper medical decision value for the target analyte; and
   after the introducing, delivering a second sample to an analytical zone of the enzymatic biosensor for determination of an amount of a target analyte in the second sample, wherein the second sample is brought into contact with the fluid in the analytical zone.

5. The process of claim 4, wherein the fluid comprises a slug comprising the target analyte, wherein the slug is delivered to the analytical zone following delivery of a wash fluid without the target analyte to the analytical zone.

6. A system for improving precision in a diagnostic test comprising:
   an enzymatic biosensor defining an analytical zone, wherein a target analyte is detectable by the enzymatic biosensor;
   a wash fluid source comprising a wash fluid, the wash fluid comprising an amount of the target analyte greater than a lower medical decision value and lower than an upper medical decision value for the target analyte;
   a first delivery mechanism in communication with the wash fluid source for introducing the wash fluid to the analytical zone;
   a second delivery mechanism in communication with a sample suspected of comprising the target analyte for introducing the sample to the analytical zone following introduction of the wash fluid to the analytical zone;
   wherein upon delivery of the wash fluid to the analytical zone and delivery of the sample, the sample contacts the wash fluid within the analytical zone prior to analysis of the sample for the target analyte, and wherein the amount of the target analyte in the wash fluid is effective to provide at least a degree of improvement in precision in the analysis for the target analyte in the sample.

7. The system of claim 6, wherein the target analyte detectable by the enzymatic biosensor is selected from the group consisting of glucose, lactate, and creatinine.

8. The system of claim 6, wherein the target analyte comprises glucose.

* * * * *